US005612180A

United States Patent [19]

Brown et al.

[11] Patent Number: 5,612,180
[45] Date of Patent: Mar. 18, 1997

[54] GENETIC FOOTPRINTING: INSERTIONAL MUTAGENESIS AND GENETIC SELECTION

[75] Inventors: Patrick Brown, Stanford; Victoria Smith, Palo Alto, both of Calif.

[73] Assignee: Board of Trustees of the Leland Stanford Junior University, Palo Alto, Calif.

[21] Appl. No.: 247,903

[22] Filed: May 23, 1994

Related U.S. Application Data

[63] Continuation-in-part of Ser. No. 62,454, May 13, 1993, abandoned.

[51] Int. Cl.[6] .............................. C12Q 1/68; C12N 15/09
[52] U.S. Cl. ............................................ 435/6; 435/172.3
[58] Field of Search ...................................... 435/6, 172.3

[56] References Cited

PUBLICATIONS

Craigie et al., "The IN protein of Moloney murine leukemia virus processes the viral ends and accomplishes their integration in vitro" Cell 62:829–837. Aug. 1990.

Jonsson et al. "Characterization of the forward and reverse integration reactions of the Maloney murine leukemia virus integrase protein purified form Escherichia coli", J. Biol. Chem. 268:1462–1469. Jan. 1993.

Lowman et al. "Affinity maturation of human growth hormone by monovalent phage display", J. Mol. Biol. 234:564–578. 1993.

Smith et al. "Genetic footprinting: a genomic strategy for determining a gene's function given its sequence", Proc. Natl. Acad. Sci USA 92:6479–6483. Jul. 1995.

Boeke et al., "Ty elements transpose through an RNA intermediate", Cell, 40:491–500 (1985).

Boeke et al., "Doubling Ty1 element copy number in Saccharomyces cervisiae: Host genome stability and phenotypic effects", Genetics, 129:1043–1052 (1991).

Boeke, "Transposable elements in Saccharomyces cerevisiae", Mobile DNA, edited by D.E. Berg and M.M. Howe, American Society for Microbiology, Washington, D. C., pp. 335–374 (1989).

Fitzgerald et al., "Rapid shotgun cloning utilizing the two base recognition endonuclease CviJI", Nucleic Acids Research, 20(14):3753–3762 (1992).

Garfinkel et al., "Transposon tagging using Ty elements in yeast", Genetics, 120:95–108 (1988).

Garfinkel and Strathern, "Ty mutagenesis in Saccharomyces cerevisiae", Methods in Enzymology, 194:342–361 (1991).

Gordon and Elliot, "Fractionation of Saccharomyces cerevisiae cell populations by centrifugal elutriation", J. Bacteriology, 129(1):97–100 (1977).

James et al., "Tests for a change-point", Biometrika, 74(1):71–83 (1987).

Kuspa and Loomis, "Tagging developmental genes in Dictyostelium by restriction enzymemediated integration of plasmid DNA", Proc. Natl. Acad. Sci. USA, 89:8803–8807 (1992).

Natsoulis et al., "Ty1 transposition in Saccharomyces cerevisiae is nonrandom", Genetics, 123:269–279 (1989).

Oliver et al., "The complete DNA sequence of yeast chromosome III", Nature, 357:38–46 (1992).

Pryciak and Varmus, "Nucleosomes, DNA–binding proteins, and DNA sequence modulate retroviral integration target site selection", Cell, 69:769–780 (1992).

Pryciak et al., "Simian virus 40 minichromosomes as targets for retroviral integration in vivo", Proc. Natl. Acad. Sci. USA, 89:9237–9241 (1992).

Ramer et al., "Dominant genetics using a yeast genomic library under the control of a strong inducible promoter", Proc. Natl. Acad. Sci. USA, 89:11589–11593 (1992).

Schmid et al., "Nucleosome disruption at the yeast PHO5 promoter upon PHO5 induction occurs in the absence of DNA replication", Cell, 71:853–864 (1992).

Schiestl and Pets, "Integration of DNA fragments by illegitimate recombination in Saccharomyces cerevisiae", Proc. Natl. Acad. Sci. USA, 88:7585–7589 (1991).

Sheseley et al., "Correction of a human $\beta^2$–globin gene by gene targeting", Proc. Natl. Acad. Sci. USA, 88:4294–4298 (1991).

Wilke et al., "Analysis of yeast retrotransposon Ty insertions at the CAN1 locus", Genetics, 123:655–665 (1989).

Primary Examiner—Jasemine C. Chambers
Assistant Examiner—Scott D. Priebe
Attorney, Agent, or Firm—Pamela J. Sherwood; Fish & Richardson P.C.

[57] ABSTRACT

Functional analysis of genes is provided by employing insertional mutagenesis to a population of DNA molecules containing the gene of interest. The DNA is subjected to a degree of insertion, where the total population of molecules provides for a substantially complete representation of insertion across the length of DNA. The DNA is then subjected to a functional selection. The effect of the selection is determined by amplifying DNA isolated from selected and control populations, and determining whether a particular region is over or underrepresented in the amplified DNA.

11 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ATAAGAATGC GGCCGCGTGC AGTCTTTCA        29

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AATGAAAGAC TGCACGCGGC CGCATTCTTA T        31

GENETIC FOOTPRINTING: INSERTIONAL MUTAGENESIS AND GENETIC SELECTION

CROSS-REFERENCE TO RELATED APPLICATIONS

This application is a continuation-in-part of U.S. patent application Ser. No. 08/062,454, filed May 13, 1993, now abandoned.

INTRODUCTION

1. Technical Field

The field of this invention is the determination of gene function.

2. Background

The use of mutants to determine gene function is a well-established experimental approach in genetics. However, the ability to correlate altered protein or DNA sequence directly with functional change had to wait for the development of DNA cloning techniques. The increasing sophistication of techniques in molecular biology now allows manipulation of DNA sequences and directed mutagenesis, where a particular residue or region can be changed, either by directing site specific nucleotide or amino acid changes, or by "scanning" mutations across a whole region.

The major drawback to analysis by existing methods is the pace at which they are conducted. Sequencing and screening individual mutants is slow and laborious, particularly when one considers how many changes can be made in the sequence of a single gene.

Ideally, one would like a method of functional analysis that allowed parallel screening of a large number of mutations at a single time. Changes in nucleotide sequence should be correlatable to the function of the gene or regulatory element. In constructing a library of mutagenized genes, the ability to direct the types of changes introduced is also desirable.

Relevant Literature

The use of the polymerase chain reaction is first described in Saiki, et al. (1985) Science 239:487. A review of current techniques may be found in Sambrook, et al. Molecular Cloning: A Laboratory Manual, CSH Press 1989, pp. 14.2–14.33.

Techniques for in vitro mutagenesis of cloned genes are known. Examples of protocols for scanning mutations may be found in Gustin, et al. (1993) Biotechniques 14:22; Barany (1985) Gene 37:111–23; Colicelli, et al. (1985) Mol Gen Genet 199:537–9 and Prentki, et al. (1984) Gene 29:303–13.

Methods for site specific mutagenesis can be found in Sambrook, et al. Molecular Cloning: A Laboratory Manual, CSH Press 1989, pp. 15.3–15.108; Weiner, et al. (1993) Gene 126:35–41; Sayers, et al. (1992) Biotechniques 13:592–6; Jones and Winistorfer (1992) Biotechniques 12:528–30; Barton, et al. (1990) Nucleic Acids Res 18:7349–55; Marotti and Tomich (1989) Gene Anal Tech 6:67–70 and Zhu (1989) Anal Biochem 177:120–4.

Descriptions of functional protein analysis utilizing in vitro mutagenesis techniques may be found in Mills, et al. (1989) J Mol Biol 205:751–64 and Ishikawa, et al. (1988) Nucleic Acids Symp Ser 1988, (19) p39–42.

A description of functional selection with phage display may be found in Matthews and Wells (1993) Science 260:1113–1117 and Lowman and Wells (1993) J. Mol. Biol. 234:564–578. The use of such information to construct a structural model of a protein is described in Jin, et al. (1994) P.N.A.S. 91:113–117.

SUMMARY OF THE INVENTION

Gene function is determined by insertional mutagenesis of DNA, followed by functional selection and a process that we term "genetic footprinting". The DNA is mutagenized such that the population of molecules will have, on average, several molecules with an insertion at any one position. The mutagenesis may result in an insertion of a sequence or in a substitution of one sequence for another. The resulting mutagenized DNA is subjected to functional selection. DNAs which encode the selected for phenotype will be over-represented whereas DNAs which do not encode that phenotype will be under-represented. DNA is isolated after selection, and compared to DNA from an unselected population. This comparison, or genetic footprinting, utilizes the specific amplification of DNA between a sequence tag at the site of the insertional mutagenesis and a known sequence at the region of interest. Differences in the representation of amplified selected DNA and of unselected DNA can be related to the nature of the selection process.

DESCRIPTION OF SPECIFIC EMBODIMENTS

The subject method provides for parallel genetic analysis to determine the function of a particular target region in a DNA coding or regulatory gene. The DNA molecule to be analyzed may be a genome, or a gene or gene fragment cloned into an episomal vector. The method provides a sensitive and reliable way to monitor the behavior of insertionally generated mutants in a large population of cells. There are three discrete, sequential steps in the process. The methodology first employs saturation mutagenesis of a population of DNA molecules. Mutagenesis is followed by selection for a phenotype corresponding to the target sequence. The polymerase chain reaction (PCR) or other system which allows for amplification of a specific sequence is then used, in conjunction with sensitive size determination for the resulting amplified DNA. Comparison of amplified DNA from a selected vs. non-selected source allows correlation of a specific region of the target DNA with its phenotype.

Each target region will comprise from 50 to 2000 nucleotides of DNA sequence. A gene may have one or more target regions, and analysis of a genome may involve several thousand target regions. After mutagenesis each target region will have at least one insertional mutation.

Any DNA sequence which provides a selectable phenotype can be analyzed by the subject methods. A phenotype is defined as the expression of genetic information, and a selectable phenotype is one for which a differential screening process can be devised. A DNA molecule comprising a cloned gene or gene fragment is a convenient vehicle for analysis, where the genetic information can be expressed in a transfected cell, or in an in vitro system. Another DNA molecule suitable for analysis is a chromosome or complete genome of microorganisms which are capable of haploid growth or easy generation of homozygous diploids The genome of prokaryotes, lower eukaryotes, particularly fungi and protista and viruses may be investigated with the subject methodology.

A wide range of selectable phenotypes exist. In most cases, the phenotype will be the result of the expression of the target DNA to provide a peptide sequence, where that peptide sequence determines the functional, i.e. structural, enzymatic, regulatory, hormonal, etc. characteristics of a protein. Structural genes, i.e. DNA sequences which encode a protein or peptide product, and regulatory genes, i.e. DNA sequences which act as regulatory regions, such as promoters, enhancers, terminators, translational regulatory regions, etc. to affect the level or pattern of gene expression are suitable for this type of analysis. When the DNA to be analyzed is a gene or fragment of a gene cloned into an episomal vector, generally the nucleotide sequence of the target DNA will be known. The subject invention may be used to analyze particular regions within a gene, so that the contribution of individual codons and amino acid residues to overall protein function can be determined. Such information is useful in the rational design of protein analogs and mimetics, and provides insight into the protein structure-function relationship.

Target DNA sequences can also be analyzed for the effect of mutagenesis of structural properties of the DNA, or complementary RNA molecules. A number of proteins are known to bind DNA and RNA. By selecting for mutations which affect the formation of nucleic acid-protein complexes, the role that particular nucleotides play in this interaction can be evaluated. Such information is useful in the rational design of DNA and RNA analogs and mimetics, and provides insight into the functional properties of DNA.

Mutagenesis of small genomes does not require that the entire sequence be determined before analysis, however partial sequence characterization of target region(s) is required in order to synthesize the appropriate primers for amplification. Contiguous nucleotide sequence of at least about 12 nucleotides, usually at least about 15 nucleotides and preferably at least about 20 nucleotides in the target region must be known in order to provide an endpoint for amplification. Target regions may be dispersed throughout the genome, chromosome or locus of interest, usually spaced not more than about 1000 nucleotides apart, more usually not more than about 500 nucleotides apart, and preferably not more than 200 nucleotides apart. A number of organisms have sufficient sequence information to meet these requirements, e.g. *S. cerevisiae, E. coli, B. subtilis*, bacteriophage λ, etc. The subject method provides information about the structure and function of gene products encoded by particular loci in the genome.

There are three discrete steps in the methodology of the subject invention. The steps are related, in that the product of one step is used as the starting material for the next step. The first step is insertional mutagenesis of the DNA at a sufficiently high level to ensure that a library of mutant DNA molecules is created where there will be at least one and preferably several molecules with an insertional mutagen in each target region to be mapped. For analysis of a DNA molecule comprising cloned genes and gene fragments it is desirable to have an insertion at every nucleotide in the target region.

For genome analysis each target region will roughly correspond to a regulatory or structural gene. It is sufficient to have at least one insertion per target region, usually at least 5 insertions per target region, and preferably at least 10 insertions per target region. Most organisms which will be analyzed by this method do not have introns. If introns are present, the level of mutagenesis will be sufficiently high that those target regions comprising a structural gene will have at least one insertion in the coding region.

The population of mutagenized DNA molecules are then subjected to at least one selective condition. The library after selection is analyzed by genetic footprinting. Genetic footprinting amplifies specific regions of the target DNA sequence from selected and unselected populations. The amplified DNA populations are separated on the basis of size with a method sensitive enough to resolve single nucleotide differences. A comparison of amplification products from the selected and unselected populations will reveal a difference in the representation of DNA molecules with insertions at particular positions within the target sequence. One can then correlate the effect of mutation at a particular residue with the selected for phenotype. Because the analysis is applied to a library of mutated DNA molecules, information about the function of a large number of residues can be obtained with a single experiment.

A number of methods can be used for saturation mutagenesis. The primary requirement is that an oligonucleotide sequence tag is inserted at the mutagenized site. The subject methods require a population of mutants to be made. After mutagenesis each individual DNA molecule in the population will have, on average, a single insertional mutation. The population, or library, of DNA molecules will include on average at least one, preferably several, independent mutations in each target sequence.

It is desirable that the mutagenesis be as close to saturating as possible. When the DNA molecule to be analyzed is a genome, saturating mutagenesis is defined as at least one sequence tag inserted in substantially every target region, usually greater than 90% of the target regions, more usually greater than 95% of the target regions. A target region will correspond to a structural or regulatory gene, with the proviso that genes longer than about 2000 base pairs in length may comprise more than one target region. A mutagenized library for analysis of a viral genome may have as few as 10 different insertions, while a library useful for analysis of a bacterial or fungal genome will have at least 10,000 different insertions.

When the DNA molecule to be analyzed is a gene or gene fragment cloned in an episomal vector, then each target region will have a large number of insertional mutations. Saturating mutagenesis is defined as at least one sequence tag inserted at substantially every nucleotide position in the target region, usually greater than 90% of the nucleotide positions, more usually greater than 95% of the nucleotide positions. A library useful for analysis will have at least about 200 different insertions for each target region.

The method of choice must allow an oligonucleotide sequence tag to be inserted into the target DNA sequence. The sequence tag may be inserted as an addition to the native sequence (insertional mutations), or may be a sequential insertion and deletion, where the sequence tag ultimately replaces the native DNA sequence (substitutional mutations). Unless specifically stated, insertional mutation will be used to refer to either method. The sequence tag may be part of the insertional mutagen or may be added in a separate, later step. In the latter case there may or may not be a net loss of sequence. It has been found that substitutional mutations where the frame of codons is unchanged from the native sequence are particularly valuable for creating highly informative mutants (see Colicelli, et al. supra). Mutants with a high informational value partially maintain their phenotype, for example proteins with reduced affinity for a substrate, temperature sensitivity, pH sensitivity, etc. instead of a total loss of function, and are especially valuable in mapping functional protein domains.

The nucleotide sequence of the tag can be any sequence which provides a unique sequence, i.e. one that is found once in the DNA molecule, for later hybridization of amplification primers. In order to prevent frameshift mutations, the tag will usually be multiples of three in length. The tag should be long enough to provide a unique tag, but short enough that usually only the function of the specific region in which it has been inserted will be disrupted. The sequence tag will usually be at least 9, more usually 12 and preferably at least 15 nucleotides in length. The tag will usually not be more than 21 and more usually not more than 18 nucleotides in length. A large tag may include lox sites, or target sequences for other site specific recombinases, restriction sites, etc. to allow excision of most of a large initial insertion to leave a small tag of the mutagen DNA. In some cases it will introduce a convenient restriction site, particularly those of type II restriction enzymes, which cleave at a site upstream or downstream from the recognition sequence.

The tag may also introduce a particular function. It may encode sequences which stabilize or destabilize α-helix or β-sheet structure. It may encode structural motifs such as sites for DNA binding proteins. Scanning mutations may use tags which encode a stretch of alanine or valine residues. Recognition sites for modification, e.g. sites for glycosylation, protease recognition, phosphorylation, methylation and the like may be included. The tag may include sequences for intracellular targeting, e.g. nuclear localization signals, etc. Sequences that encode an immunogenic epitope for recognition by antibodies, T cell receptors, etc. may be included. To facilitate later purification steps, sequences such as oligohistidine tags may be included.

The actual method for mutagenesis will depend on the type of target DNA to be analyzed. While the frequency of insertions, sequence tags, etc. as described above are the same for all types of DNA, it is convenient to consider the mutagenesis of small genomes, such as that of *S. cerevisiae*, separately from the mutagenesis of cloned genes and gene fragments.

For mutagenesis of genomes, certain conditions must be met. In order to efficiently perform the genetic footprinting step, the genome will usually be less than about $10^8$ bp in size, preferably less than about $5 \times 10^7$ bp in size, and may be less than about $1.5 \times 10^7$ bp in size, or smaller. A viral genome will usually be greater than $10^3$ nucleotides in length, while a bacterial genome will usually be greater than $10^5$ bp in length. When the method of selection will be screening for loss of function, the target host cell will be capable of growth as a haploid or easy generation of homozygous diploids. This is not required if screening for dominant mutations, such as over-expression of a protein.

Conveniently, where a retroviral or transposable element is available, such element may be used for insertional mutagenesis. In many cases the insertion element can be delivered by infection, e.g. with a retrovirus or bacteriophage. In other cases induction of transcription of a transposable element already resident in the host cell is most convenient. In the latter method, the element is provided with an inducible promoter, so that replication of the element may be greatly enhanced under the inducible conditions. The inducible promoter will be functional in the target host, where the host is cellular. The insertional element will comprise the sequence tag for amplification. With an insertional element, a large number of cells, usually at least about $10^{10}$, preferably at least about $10^{12}$, and usually not more than about $10^{15}$, will be grown in a non-inducing complete liquid medium after introduction of insertional elements into the cells. The manner of introduction can be any convenient means which provides for a high efficiency of introduction into the target host. Once the cell population has been grown, the cells may then be transferred to an inducing medium, which will induce the integration of the insertional element. Growth in the medium may be continued for sufficient time to allow for an accumulation of a minimum number of insertions per cell, which minimum number will be related to the size of the genome, efficiency of integration, and the like. The insertional element may include a marker for selection, so as to select for cells having the insertional element. Markers will usually include antibiotic resistance.

Other methodologies for insertional mutagenesis may be associated with identifying open reading frames (ORF's) whose overexpression affects a cell's behavior in the screening process. By carrying out the initial mutagenesis using an element carrying a strong inducible promoter or enhancer element and then subjecting the insertionally-mutagenized cells to each selection under both inducing and non-inducing conditions, one may be able to identify the effect of overexpression of a sequence.

In many genetic tests with sporulating hosts, e.g. yeast mutagenized with a transposable element, it may be preferable to do the initial mutagenesis in a diploid strain, then sporulating, purifying haploid spores, and then subjecting the haploid progeny to an array of genetic tests. This approach has the advantage that there will be little selection against recessive lethals in the diploids, so that the transposition can be induced for many generations, allowing more insertions per cell, and the diploid cells can be amplified, if needed, after mutagenesis. The disadvantage is that a defect in spore germination precludes other assays, and this cannot be distinguished from other defects. This complication may be complemented by data from the haploid mutagenesis procedure.

Following mutagenesis of a genome it is generally not necessary to isolate the library of different mutated DNA molecules or to introduce the DNA into a different host cell. The population of cells after mutagenesis can conveniently be directly screened for the effect of different selective conditions.

Methods for the insertional mutagenesis of DNA molecules comprising genes or gene fragments cloned into episomal vectors involve generating random breaks in a circular DNA molecule coupled to, or followed by ligation of an insertion sequence to the newly formed termini. The insertion sequence may comprise the sequence tag, or may be an intermediate which will be replaced by the sequence tag. The DNA molecule to be analyzed will comprise at least one target region. A target region will be at least about 100 nucleotides in length, more usually at least about 200 nucleotides, and preferably at least about 500 nucleotides, usually not more than about 5000 nucleotides in length, more usually not more than 2000 nucleotides. In addition to the target region(s), flanking sequences of vector sequences, regions contiguous on the native chromosome, etc. may also be present in the DNA molecule.

It is desirable to introduce breaks randomly, with a method which does not act preferentially on specific sequences. Methods are also useful which preferentially react at specific sequences but are able to introduce breaks at greater than about 90% of the nucleotide positions in a population of DNA molecules. Methods for introducing random breaks or nicks in DNA include reaction with Fenton reagent to produce hydroxyl radicals and other chemical cleavage systems, integration mediated by retroviral integrase, partial digestion with an ultra-frequent cutting restriction enzymes, partial digestion of single stranded DNA with S1 nuclease, partial digestion with DNAse I in the presence of $Mn^{++}$, etc.

The insertion sequence may be ligated blunt to blunt ends with the cleaved DNA, or a degenerate overhang on the insertion sequence may be used to hybridize to the cleaved DNA. The insertion sequence may be present as a single- or double-stranded oligonucleotide, and may include lox or type IIs restriction endonuclease recognition sites. After insertion and ligation, the mutagenized molecule is then recircularized, and expanded by biological replication, in vitro amplification, etc.

In many cases it is desirable to convert an insertion mutation into a substitution, so that there is no net change in the length of the target region. It has been found that substitution mutation are often more informative than insertion or point mutations. This is accomplished by replacing the original insertion sequence, along with a defined length of target DNA, with a sequence tag. This may conveniently be performed by providing a recognition site for a type IIs in the insertion sequence. The type IIs endonuclease will cleave the DNA at a site distant from its recognition site, thereby creating a hole of defined size in the target region. The hole is filled by ligation of the sequence tag to the newly created termini. The sequence tag is designed to precisely replace the number of base pairs in the hole. After expansion by biological replication, in vitro amplification, etc. the mutagenized gene can be analyzed in the primary vector, or recloned into a suitable expression vector.

As an illustration of a method for insertional mutagenesis, a target DNA sequence is inserted into an episomal vector which allows isolation of the DNA in a single stranded circular form, such as M13 mp19 or pBluescript™. The vector is transfected into *E. coli*, from which DNA is then isolated. In the case of single-stranded phage vectors, viral DNA is isolated from the chimeric phage. Single strand nicks are introduced into the circular plasmid molecule by the addition of DNAse I. Full length linear single stranded molecules are isolated by gel electrophoresis. A double stranded oligonucleotide consisting of the desired sequence tag for insertion with an additional degenerate (256 fold) 4-base 3' overhang is added. The degenerate overhang hybridizes to complementary termini 3' of the linear single-strand, allowing its ligation to the sequence tag. The ligation product is isolated and fresh oligonucleotide exactly complementary to the sequence tag added. DNA polymerase is used to extend from the oligonucleotide to obtain full-length blunt-ended double-stranded linear DNA molecules. The DNA is circularized by ligation at dilute concentration. Primers which are specific for the sequences just outside of the sequence which is to be analyzed are used for amplification by the polymerase chain reaction (PCR). The amplified sample of DNA molecules contains a library of mutations. The sample is then cloned into an expression vector, which is transfected into host cells for use in the functional screening.

An alternative method for insertional mutagenesis of DNA fragments, described in detail in the experimental section, utilizes the integrase protein of a retrovirus, e.g. mouse leukemia virus (MLV), human immunodeficiency virus (HIV), avian leukemia virus (ALV), rous sarcoma virus (RSV), etc. to mediate the insertion of oligonucleotide primers at random sites in a target DNA. A library of mutagenized DNA molecules is created where the only difference between them is the site at which the DNA is integrated.

In order to perform the next step of the subject method with target DNA sequences cloned into an episomal vector, the library of mutagenized DNA molecules will be introduced into a suitable assay system. For analysis of protein function the library will be in a vector which allows for expression of the gene product, and will be transfected into suitable host cells. The host cells can be any prokaryotic or eukaryotic cells which normally express the gene of interest, or can be other cell types with established expression systems. For example, a number of mammalian proteins have been shown to function in yeast cells. The ease of manipulation and growth of single-celled organisms, e.g. bacteria, fungus, protista, etc. make them advantageous as host cells.

After the target DNA is mutagenized, functional selection is performed. Any method that selectively recovers a nucleic acid based on some property of that molecule, or its encoded product can be used. It is required that, after selection, the representation in the library of at least one mutant, usually at least 5–10 or more mutant DNAs will be changed, compared to the unselected library.

Functional screening can be any method that selects for cells with a particular phenotype. The simplest example will be selection for cells which can grow in a medium which is deficient in a nutrient required for growth, such as medium which lacks an amino acid. A host cell which is deficient in metabolism of a particular amino acid will be transfected with a mutagenized library of DNA clones containing the gene which complements the defect. The cells are then grown in media lacking the amino acid. After several rounds of cell division, host cells carrying a gene which is mutagenized in a region critical for gene function will be under-represented in the population, whereas cells carrying a gene which complements the metabolic defect will be over-represented.

A similar screen can be devised for determination of the function of regulatory regions in DNA. Mutagenesis of a promoter or enhancer region can be coupled to expression of a gene which provides for a selective advantage, such as antibiotic resistance, HAT selection, etc. The host cells are grown in medium containing a cytotoxic reagent, where expression of the gene encoding resistance is regulated by the target DNA. Mutations in essential promoter or enhancer regions may reduce expression of the resistance protein, resulting in reduced representation of those cells.

Cell growth is not necessarily the basis for the functional screen. Methods for processing large numbers of cells, such as flow cytometry, magnetic bead selection, etc. are known in the art. For example, to determine the effect of mutation on a protein's three dimensional structure one can screen with an antibody which recognizes a conformational epitope of the protein. Host cells are induced to express the protein on the cell surface, using native or introduced sequences. Labeled antibodies are added to the cells, and processed by fluorescence activated cell sorter (FACS). Those cells carrying DNA mutations which disrupt the protein three dimensional structure will bind the antibody with varying degrees of affinity, and, depending on the sort parameters, can be over- or under-represented in the sorted population. Site specific DNA binding proliferation may also be used as the basis for selection.

A phage display system, described for example in Lowman and Wells (1993) J Mol Biol 234:564–78, can be used to select phage particles based on binding or activity. The mutagenized target DNA sequence is cloned into a filamentous bacteriophage vector, e.g. M-13, fd, f1, etc. with suitable regulatory sequences for efficient expression of the target DNA. A fusion protein may be made with the target DNA and the anchor portion of phage coat protein. In most cases the phage vector will require helper phage to be present for efficient replication. The phage vector is used to infect a suitable host bacteria, for example *E. coli* for M-13. The phage are allowed under replication, and produce particles with the protein encoded by the target DNA "displayed" on the surface. The phage can then be selected for binding characteristics to a substrate, ligand, antibody, etc.

After the selection process, one has a population where the mutagenized DNA molecules are not equally represented. The mutants where there are disrupted regions of the DNA sequence essential for the selected phenotype will be selected against in the functional screening process. Therefore, cells carrying those DNA molecules will be under-represented in the selected population. Conversely, mutants which provide or enhance expression of the phenotype will be over-represented in the selected population.

As a control, one has a population of cells which are not subjected to the functional selection. In this population, the original library of mutagenized DNA molecules should be equally represented. The control population and the selected population are used to make a genetic footprint, which will determine which mutated DNA molecules have been selected for, or against. This is done by amplifying specific DNA regions, and comparing the two populations. DNAs which are present in the control, but depleted from the selected population correspond to those DNAs where the selected phenotype was disrupted. DNAs which are present in the control, but over-represented in the selected population correspond to those DNAs where the selected phenotype was provided or enhanced.

When the target DNA is a genome, once sufficient DNA from cells subjected to the various sets of selective conditions has been obtained, no further manipulation of the host is required, since subsequent functional analyses of DNA sequences can be carried out by PCR and gel electrophoresis. In effect, thousands of insertion mutations in each gene of interest can be tested retrospectively for their effects on the complete battery of tests. The primers, once synthesized for a given test sequence, can also be archived, so that when a new functional selection is developed, all of the existing primers can be retested using the resulting DNA.

The polymerase chain reaction (PCR) is exemplary of an amplification procedure useful in footprinting. PCR specifically amplifies a region of DNA lying between two designated sequence endpoints. A primer which hybridizes to the insertional mutagen's sequence tag provides for one end point. An arbitrary unique sequence in the target region is chosen to be the second endpoint. The endpoint will be a unique sequence at least about 12 nucleotides in length, usually at least about 15 nucleotides and preferably at least about 20 nucleotides. Each target sequence will have an endpoint. The length of DNA between the sequence tag and endpoint will defined by the distance which can be amplified, usually less than 2000 nucleotides, more usually less than 1000 nucleotides, and preferably less than 500 nucleotides. There are no particular constraints on the exact nucleotide sequences chosen for the endpoint, although it is preferable to avoid sequences with significant secondary structure, or which are particularly A-T or G-C rich. One of the primers may be labeled, for example with a radioactive or fluorescent tag, for later analysis.

Amplification of a mixed population of DNA molecules, i.e. one where the insertional mutagen is randomly inserted, will yield a composition containing DNA molecules of discrete lengths. As described above, one end point will be the insertional mutagen sequence tag, and the other will be a fixed point in the gene. A set of nested molecules extending out from that fixed point are generated.

Alternatively, where the inserted sequence is too short to provide for effective PCR amplification, the mutagenized sequence can be amplified by PCR using flanking primers. The position of insertions in the resulting amplified population of DNA molecules is analyzed by primer extension, using a driver corresponding to the inserted sequences and extending it to the end of the amplified fragment using a DNA polymerase. The resulting fragments have lengths that precisely reflect the positions of the inserted sequence in the population of DNA molecules.

The DNA from unselected or non-selective growth conditions will have all members of that set of nested molecules present. If the region of insertionally mutagenized DNA is 300 nucleotides in length, then there will be up to 300 discretely sized DNAs, each corresponding to an insertional mutagen at a specific site. DNA samples from cells subjected to functional selection will be depleted of amplified DNA corresponding to those insertions that disrupt functions essential for surviving the selection.

DNA is conveniently analyzed by gel electrophoresis, for which sensitive size fractionation methods are well-known. After electrophoresis one will see the nested amplified DNAs resolved into a pattern of distinct bands, each band representing the DNA of a single size. High resolution gels are easily capable of resolving differences of a single nucleotide in length. Particularly, with an ABI sequencer, one can employ different fluorescent labels, and multiplex samples, allowing four samples to be analyzed in a single lane, with 144 samples analyzed per gel run.

Gel electrophoresis will show a "ladder" with a band (which may also be represented as peaks on a graph) present for every nucleotide where the insertional mutagen is present. However, after selection, some molecules will be under- or over-represented in the source DNA. Size fractionation will show a "footprint" or reduced signal from bands in a particular region. Both the number and intensity of bands are indicative that host cells carrying the gene were selected for or against. The boundaries of the "footprint" will roughly identify the boundaries of the function in question. For each run for tests that appear informative, repeat analysis may be used from the unselected sample as an internal standard, providing for accurate quantitation. Because the only variable in the construction of the mutants is the position of the inserted sequence, which can be inferred precisely from the migration of the corresponding band upon gel electrophoresis, the precise nucleotide sequence of each mutant can be assigned based on the band's position. Thus the laborious process of sequencing each mutant molecule individually is avoided.

If the representation of a test sequence in the library appears significantly altered by the selection, one may wish to confirm the results. Since the sequence of each mutant can be inferred from the electrophoretic migration of the corresponding band, the sequence can be reconstructed by standard synthetic and cloning methods, confirmed, and directly retested in the selection process.

The following examples are offered by way of illustration and not by way of limitation.

EXPERIMENTAL

Example I

Genetic Footprinting of a Yeast Genome

A genetic map of much of the yeast genome has been constructed, and the DNA sequence partially determined. However, there are large stretches of chromosomal DNA which are apparently coding sequences for unknown proteins. The subject methods are particularly useful for assigning functions to the products of these genes. The entire genome is mutagenized, and the cells are then subjected to a number of selective conditions.

S. cerevisiae yeast cells [GRF167(MATa his3Δ200 ura3-167 GAL$^+$)] bearing Ty1 (a galactose-inducible Ty1 element, carrying a synthetic linker inserted close to one end of the delta element modified from a construct provided by Dr. Jef Boeke; plasmid pPBTy1) or Ty2 plasmid (marked with a neomycin phosphotransferase gene provided by Dr. David Garfinkel) were maintained at a cell density of $1 \times 10^6$ to $2 \times 10^7$ in (−uracil) (+galactose) liquid medium for a period of 4 days at 24° C. Following induction, $2 \times 10^8$ cells were grown in rich (YPD) or minimal medium for varying numbers of generations. DNA was prepared using standard methods (zymolyase/SDS-heat/isopropanol precipitation).

PCR analysis was performed using Taq polymerase (Cetus) on 0.8–1.0 μg of DNA with an unlabeled Ty-specific oligonucleotide and fluorescein-labeled gene-specific oligonucleotide. PCR products were size-fractionated on 1×TBE 6% polyacrylamide gels and the fragments detected by laser excitation using an Applied Biosystems 373A automated DNA sequencer. The oligonucleotide for Ty2 primes close to the 3' end of the inserted neomycin phosphotransferase gene; therefore, all PCR products which represent genuine insertions should be greater than approximately 350 bp in size. The Ty1 oligonucleotide primes to the unique polylinker region (SSB) and therefore produces fragments of approximately 30 bp and greater. The sequencing software of the ABI sequencer does not necessarily size these peaks correctly and approximate sizes were estimated from M13 T-tracks.

PCR analysis at LYS2 from cell grown for 15 generations in rich (A) and minimal (B) medium was performed using the Ty2-neo primer. The LYS2 primer is located about 330 bp into the LYS2 coding sequence, directed upstream. Approximately 10 large peaks of greater than 350 bp in size were present in the rich medium sample but absent in the minimal medium sample.

Following the above procedure, the following experiments were carried out. PCR at LYS2 using Ty2-neo and two different LYS2 primers was performed: A, the 330 bp primer from above; B, a primer located at approximately 430 bp in the LYS2 coding sequence. The DNA was from cells grown in rich medium for 15 generations. Most of the major peaks were still present with LYS2 primer 2, but shifted in size by about 100 bp.

The next PCR analyzed the LEU2 using Ty2-neo on two different DNA samples, both taken from samples grown for 15 generations in rich medium. The LEU2 primer is located about 350 bp into the LEU2 coding sequence. The first four major peaks are located in the coding sequence and the last three peaks in the promoter region. The pattern was consistent between the different DNA samples and appeared to be consistent between samples from different Ty inductions. Repeating the above analysis using a second LEU2 primer located at about 450 bp into the coding sequence, revealed the same pattern of peaks shifted by approximately 100 bp.

Example II

Mutagenesis of a Yeast Genome by Partial Digestion

Alternative methods for insertional mutagenesis to the transposable element include partial digestion of the genome using an ultrafrequent cutting enzyme, e.g. CviJ1 under "2-star conditions" (Fitzgerald et al. [1992]), allowing cleavage approximately every 50 bp). DNA is isolated from S. cerevisiae yeast cells [GRF167(MATa his3Δ200 ura3-167 GAL$^+$)] and incubated with CviJ1. Aliquots of the digestion are removed at five minute intervals, and fractionated by gel electrophoresis to determine the extent of digestion. An incubation period which provides fragments of about 2 kb is chosen.

The digested DNA is treated with alkaline phosphatase to remove terminal phosphate groups. Complementary primers 20 nucleotides in length, encoding a unique sequence tag with stop codons in all reading frames and a recognition site for Not I are added to the digested DNA in the presence of T4 DNA ligase, ligation buffer and ATP. The reaction mix is incubated overnight at 4° C., then heated, diluted 1:100 in ligation buffer and recircularizing by ligation.

The circular DNA is digested with Not I, and the fragments cloned in a high-copy plasmid having the S. cerevisiae URA 3 gene, which is capable of complementing [GRF167(MATa his3Δ200 ura3-167 GAL$^+$)] yeast cells. A library of at least about $10^6$ independent clones is collected and subjected to minimum amplification. DNA from this library is then cut using Not I, which cuts in the linker used previously for circularization. The ura3-167 yeast strain is transformed with the library, and selected for growth in uracil deficient medium. Homologous recombination occurs between the fragments originally cloned from the yeast DNA, and the host genome, which results in disruption of the gene as a result of insertion of the plasmid vector. A sufficient number of transformants are selected, e.g. $10^6$, and the initial colonies from platings are screened and footprinted as described in Example I.

Example III

Mutagenesis of a Yeast Genome by Endonuclease Mediated Insertional Mutagenesis

An alternative method of mutagenesis uses restriction endonuclease mediated insertional mutagenesis as described in Schiestl and Petes (1991) PNAS U.S.A 88:7585–9; and Kuspa and Loomis (1992) ibid 89:8803–7.

A 100 bp DNA fragment containing EcoR1 compatible ends, and a sequence tag encoding a unique sequence tag with stop codons in all reading frames is synthesized and cloned into a high copy number plasmid. The plasmid is expanded, and the fragment isolated by gel electrophoresis.

[GRF167(MATa his3Δ200 ura3-167 GAL$^+$)] yeast cells are transfected with EcoR1 and the 100 bp fragment. Insertion of the DNA fragment occurs at diverse genomic sites corresponding to the recognition sequence of the restriction enzyme. The transfected yeast cells are briefly grown in rich media to expand the population. The cells are then screened and footprinted as described in Example I.

Example IV

Analysis of Retroviral Function

To determine the effect of mutation on viral replication, a comprehensive library of mutants carrying a single mutation, consisting of the insertion of a specific short nucleotide, from 9 to 18 bases, is created. The oligonucleotides are a multiple of 3 bases in length in order to maintain reading frame. Each distinct mutant is represented many times (greater than about $10^2$) in the population and insertions between any two adjacent bases in the target sequence are approximately uniformly represented.

Insertional mutagenesis

A plasmid clone of the integrase gene from Moloney Leukemia Virus is used as the target for mutagenesis. Closed circular plasmid DNA is isolated. Single stranded nicks are introduced into the circular molecule by reaction with Fenton reagent to produce hydroxyl radicals, as described in Dixon, et al. (1991) *Methods in Enzymology* 208:380–413. The resulting products have lost one base and retained the flanking 3' and 5' phosphates. The nicked molecule is then reacted with polynucleotide kinase to remove the 3' phosphate, as described in Richardson, C. C. (1981) in *The Enzyme* (P. Boyer ed.) Vol. 14, pp. 299–314, Acad. Press, San Diego.

The DNA is then denatured by heating. The samples are quenched on ice, and electrophoresed on an agarose gel. The linear full-length molecules are isolated from the gel. A double-stranded oligonucleotide consisting of the sequence tag for insertion with an additional degenerate (256 fold) 4-base 3' overhang is then added in excess and ligated to the 3' ends of the linear single strands.

The ligation products are isolated from the oligonucleotides by column chromatography. Fresh oligonucleotides which are exactly complementary to the sequence tag are added. *T. litoralis* DNA polymerase and deoxynucleotides are added to synthesize the complementary strand. Full-length blunt-ended double-stranded linear DNA molecules are the result of the polymerase reaction.

The double-stranded linear products are ligated at dilute concentration to circularize, and then the circular products are isolated by gel electrophoresis. The mutagenized MLV integrase gene is then isolated from the circular products by digesting with restriction endonuclease and cloning into a plasmid vector. The construct is transfected into *E. coli* and grown for several generations. The plasmid DNA is isolated, and the mutagenized integrase gene cut out of the plasmid and ligated into a cloned MLV proviral genome.

Retroviral Packaging and Reinfection

The library of mutant proviral clones is introduced into a mammalian cell line so that the proviruses can be expressed, virus particles assembled and used for infection. The library is transfected into the helper cell line ψCRE. Packaged virus is harvested, and used to reinfect a second cell line at an MOI of less than 1. Virus particles are harvested early after transfection, when helper-encoded proteins are in greatest excess over proteins encoded by the transfected proviruses in order to minimize dominant-negative effects.

24 hours after infection, the infected cells are stained with FITC conjugated antibodies specific for the MLV envelope protein. The stained cells are sorted by flow cytometry to isolate cells which are productively expressing the viral envelope, to obtain at least about $10^5$ founder cells. These cells are used as the source of mutant viruses for further analysis.

Integrase functional selection

For each function to be analyzed, a pool of mutant viruses representing with high redundancy the entire library of mutants, is used to infect cells at an MOI of less than 1. After infection, the cells are harvested at an appropriate time and fractionated into nuclear and cytoplasmic fractions. Each subcellular fraction is further fractionated by Hirt fractionation, sucrose gradient sedimentation or tested in an assay. The nucleic acid in selected fractions is isolated and in some cases is treated with selective enzymes such as RNAses or DNAses and further fractionated by gel electrophoresis, so as to isolate nucleic acids corresponding to the specific replication intermediates: intracellular viral genomic RNA, DNA synthesis intermediates, full-length linear DNA with recessed ends, etc. Each isolated sample of RNA or DNA will correspond to a specific stage of the life cycle and will represent the genomes of viruses that were able to complete all preceding steps in the infection process. Genomes of mutant viruses that were unable to complete any of the preceding steps in the process will not be represented in the nucleic acid obtained in any later stage of the process.

PCR amplification

PCR is used to determine which mutants are represented in each DNA or RNA sample. The mutants are marked by an insertion of a specific defined oligonucleotide sequence tag and the analysis is carried out using an unlabeled primer corresponding to the sequence tag and a labeled primer corresponding to a defined sequence in the normal viral genome. Each insertion downstream of the labeled primer gives rise to an amplified product whose size will precisely define the site and sequence of the corresponding mutation. Those mutations, represented by a particular RNA or DNA sample, which result in the failure to reach a specific state in the virus life cycle result in the absence of the corresponding band from the PCR products.

Gel electrophoresis on ABI sequencer

The products of the polymerase chain reaction are run on ABI sequencer. The resulting analysis shows an absence of amplified DNA peaks corresponding to insertions at the site of critical residues for integrase function.

Example V

Functional Analysis of Retroviral Gag Proteins

In order to determine critical regions for function in the DNA encoding MLV gag proteins, the analysis is performed as described in Example IV, using the gene encoding gag as a target sequence.

Example VI

Insertional Mutagenesis Mediated by MLV Integrase Protein

The reaction mediated by retroviral integrase inserts exogenous DNA at random sites in the target DNA, and can be performed in vitro (Craigie, et al. [1990] Cell 62:829–837 and Jonsson, et al. [1993] J. B. C. 268:1462–1469). Virtually all sites in a DNA molecule can be used by the enzyme for integration (Pryciak and Varmus [1992] Cell 69:769–780). After integration, a population is obtained of linear molecules with inserted DNA at each terminus. Conveniently the inserted DNA is a pair of complementary oligonucleotides, as exemplified by SEQ ID NO:1 and SEQ ID NO:2. The pair of primers is joined to each terminus of the target DNA. The 3' end of the primer is joined to 5' phosphates, staggered by 4 base pairs, in the target DNA, resulting in gaps flanking the newly-integrated DNA. The DNA is then manipulated to delete the inserted DNA, and replace it with the oligonucleotide sequence tag such that there is no net change in the number of nucleotides present in the target sequence.

The DNA sequence is converted into a circular form by intramolecular ligation by cloning the sequence into a vector capable of forming a circular structure. The circular DNA is added to a mixture of MLV integrase and the oligonucleotide primers:

[SEQ ID NO:1] 5' ATAAGAATGCGGCCGCGTGCAGTCTTTCA 3'

[SEQ ID NO:2] 3' TATTCTTACGCCGGCGCACGTCAGAAAGTAA 5'

The primers contain the recognition sequence for MLV integrase, for Not I restriction endonuclease, and for Bsg I restriction endonuclease. Because the integration reaction joins only the 3' terminus of the oligonucleotide to a 5' phosphate group in the target DNA, the products of the reaction will have single-stranded gaps flanking the 3' termini of the of the disrupted target DNA.

To convert to gap-free linear molecules, the integration products are incubated with Taq polymerase in the presence of dATP, dTTP, dGTP and dCTP. The resulting filled in molecules are amplified in a polymerase chain reaction using the primer [SEQ ID NO:1]. Only molecules that have the oligonucleotide primers joined to each end will be exponentially amplified.

The linear amplified circularly permuted molecules are redrcularized by ligation at a low DNA concentration to prevent formation of concatamers. Selection and genetic footprinting can be performed on this population of molecules using [SEQ ID NO:1] and [SEQ ID NO:2] as a sequence tag.

Conversion of an Insertion Mutation to a Substitution

The information content is usually higher for substitution mutations than for insertion mutations. The following method is used to convert the population of mutants described above to a population of substitution mutants.

The circular DNA is digested with Bsg I, which recognizes a site in [SEQ ID NO:1] and [SEQ ID NO:2]. The enzyme creates a staggered cut 6 bases into the target DNA, creating a double stranded gap of twelve bases, with a 2 base overhang at each 3' terminus. A double-stranded oligonucleotide consisting of the 12 base pair sequence tag for insertion with an additional degenerate (256 fold) 2-base 5' overhang is then added in excess and ligated only to the 5' ends of the linear single strands.

The reaction mix is heated, and the unligated oligonucleotides melted off. Polynucleotide kinase and ATP are added to phosphorylate the termini, and ligase is added to recircularize the molecule.

The resulting population of DNA molecules contains a substitution of 12 base pairs of the target sequence with 12 base pairs of an oligonucleotide sequence tag. The substitution occurs at random sites throughout the target sequence, so that the effect of the substitution at every position can be determined by functional selection and genetic footprinting as described in Example II.

Example VII

Genetic Footprinting of Affinity Selected Human Growth Hormone

A selection process for construction of high affinity variants of human growth hormone for binding to its receptor has been previously described (H. Lowman and J. Wells [1993] J. Mol. Biol. 234:564–578). An alternative method of determining residues critical for binding is performed as follows.

Insertional mutagenesis is performed as described in Example VI, using MLV integrase as a means to randomly mutagenize the gene encoding human growth hormone. The target plasmid phGHam-g3, which encodes wild-type hGH fused to the carboxy terminal domain of M13 gene III, is described in Lowman, et al. (1991) Biochemistry 30:10832–10838. The fusion protein is expressed on the surface of M13 phage. After integration of the primers [SEQ ID NO:1] and [SEQ ID NO:2] with integrase, the resulting linear molecule is recircularized.

The circular DNA is digested with Bsg I, which recognizes a site in [SEQ ID NO:1] and [SEQ ID NO:2]. The enzyme creates a staggered cut 6 bases into the target DNA, creating a double stranded gap of twelve bases, with a 2 base overhang at each 3' terminus. A double-stranded oligonucleotide consisting of a 12 base pair sequence tag encoding a stretch of alanine residues, with an additional degenerate (256 fold) 2-base 5' overhang is then added in excess and ligated only to the 5' ends of the linear single strands. The reaction mix is heated, and the unligated oligonucleotides melted off. Polynucleotide kinase and ATP are added to phosphorylate the termini, and ligase is added to recircularize the molecule.

The resulting library of DNA molecules is subjected to functional selection. Phagemid particles that display a single copy of the of the hGH-gene II fusion protein are prepared by electro-transforming $E.$ $coli$ XL1-Blue cells (from Stratagene®) and adding M13K07 helper phage (described in Vieira and Messing [1987] Methods Enzym. 153:3–11) which provides a large excess of the wild-type gene III protein. The particles are prepared and selected for binding to the hGH receptor as described in Lowman, et al. supra.

After undergoing 2 to 7 cycles of selection, DNA is isolated from the phage particles. PCR analysis is performed using Taq polymerase (Cetus) on 0.8–1.0 µg of DNA with unlabeled oligonucleotide complementary to the sequence tag and fluorescein-labeled M13 gene III-specific oligonucleotide. PCR products are size-fractionated on 1×TBE 6% polyacrylamide gels and the fragments detected by laser excitation using an Applied Biosystems 373A automated DNA sequencer.

Analysis of the PCR amplification products shows a footprint, or depletion of peaks, corresponding to insertions at residues which are critical for hGH binding to its receptor.

It is evident from the above results, that the subject methodology provides for an efficient way to screen the effect of insertional mutation on a target DNA sequence. By subjecting a library of mutated target DNA molecules to a selective condition or conditions, one can define the nature of the target sequence. Large amounts of information can be obtained which correlate the structure and function of coding or regulatory DNA sequences with the target nucleotide sequence.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for functional analysis of a target region in a genome of a microorganism which grows as a haploid, said method comprising:

mutagenizing said genome by insertion of a sequence tag to provide a population of cells wherein at least 90% of target regions in the genomes of said population of cells contains a sequence tag insertion;

subjecting a first aliquot of said population of cells to at least one selective condition and a second aliquot to a non-selective condition to provide at least one selected and one non-selected aliquot;

amplifying target region DNA from said at least one selected and one non-selected aliquots, wherein said amplification is by polymerase chain reaction using a first primer hybridizing to said sequence tag and a second primer hybridizing to a known endpoint, said endpoint being characterized as an arbitrary unique sequence in said target region, to provide amplified DNA; and resolving by gel electrophoresis said amplified DNA from said at least one selected and one non-selected aliquots into individual bands differing by size to identify the position of individual sequence tag insertions within said target region, whereby differences in the presence or intensity of bands between said at least one selected and one non-selected aliquots are indicative that said sequence tag insertion causes a difference in response to said selective condition employed with said at least one aliquot, resulting in the functional analysis of said target region.

2. A method according to claim 1, wherein mutagenizing is performed with a transposable element.

3. A method according to claim 2, wherein said target DNA comprises a gene encoding a protein.

4. A method according to claim 1, wherein said selective condition is growth of cells in media lacking a nutrient that is an intermediate in a metabolic pathway.

5. A method for functional analysis of a target region in a sequence of interest, said method comprising:

mutagenizing said target region by insertion of a sequence tag to provide a population of DNA molecules containing a sequence tag insertion in at least 90% of nucleotide positions in said target region;

introducing said population of mutagenized DNA molecules into host cells that express said sequence of interest;

subjecting a first aliquot of said host cells to at least one selective condition and a second aliquot to a non-selective condition to provide at least one selected and one non-selected aliquot;

amplifying target region DNA from said at least one selected and one non-selected aliquots, wherein said amplification is by polymerase chain reaction using a first primer hybridizing to said sequence tag and a second primer hybridizing to a known endpoint, said endpoint being characterized as an arbitrary unique sequence in said target DNA, to provide amplified DNA; and resolving by gel electrophoresis said amplified DNA from said at least one selected and one non-selected aliquots into individual bands differing by size to identify the position of individual sequence tag insertions within said target region, whereby differences between the presence or intensity of bands between said at least one selected and one non-selected aliquots are indicative that said sequence tag insertion causes a difference in response to said selective condition employed with said at least one selected aliquot resulting in the functional analysis of said target region.

6. A method according to claim 5, wherein mutagenizing comprises the steps of:

combining DNA comprising said target region with retroviral integrase and a first set of complementary oligonucleotide primers, said primers comprising (a) a recognition sequence for said retroviral integrase and (b) a sequence tag, wherein said retroviral integrase mediates the insertion of said first set of complementary oligonucleotide primers to provide a population of mutagenized DNA molecules.

7. A method according to claim 5, wherein mutagenizing comprises the steps of:

combining DNA comprising said target region with retroviral integrase and a first set of complementary oligonucleotide primers, said primers comprising (a) a recognition sequence for said retroviral integrase and (b) a recognition site for a type IIs restriction endonuclease, wherein said retroviral integrase mediates the insertion of said first set of complementary oligonucleotide primers to provide a population of mutagenized DNA molecules cutting said population of mutagenized DNA molecules with said type IIs restriction endonuclease to provide cut DNA; and ligating to said cut DNA a second set of complementary oligonucleotide primers comprising a sequence tag.

8. A method according to claim 5, wherein said sequence of interest comprises a gene encoding a protein.

9. A method according to claim 8, wherein said population of mutagenized DNA molecules are cloned into a filamentous bacteriophage vector with regulatory sequences for expression of said sequence of interest.

10. A method according to claim 5, wherein said sequence of interest comprises a regulatory gene.

11. A method according to claim 10, wherein said selective condition is growth in media containing a cytotoxic agent, and said regulatory gene controls expression of a gene conferring resistance to said cytotoxic agent.

* * * * *